(12) United States Patent
Desmurs et al.

(10) Patent No.: US 6,399,820 B2
(45) Date of Patent: Jun. 4, 2002

(54) PROCESS AND REAGENT USEFUL FOR THE SYNTHESIS OF SULPHANILIDE WHICH IS PERHALOGENATED ON THE CARBON BORNE BY THE SULPHUR ATOM OF THE SULPHANILIDE FUNCTION

(75) Inventors: Jean-Roger Desmurs, St-Symphorien D'Ozon; André Millet, St-Laurent de Mure; Virginie Pevere, Lyons, all of (FR)

(73) Assignee: Rhodia Chimie, Boulogne Billancourt Cedex (FR)

( * ) Notice: Subject to any disclaimer, the term of this patent is extended or adjusted under 35 U.S.C. 154(b) by 0 days.

(21) Appl. No.: 09/859,016

(22) Filed: May 15, 2001

Related U.S. Application Data

(63) Continuation of application No. 09/433,436, filed on Nov. 4, 1999, now Pat. No. 6,271,419.

(30) Foreign Application Priority Data

Nov. 4, 1998 (FR) ............................................. 98 13863
Oct. 6, 1999 (FR) ............................................. 99 12453

(51) Int. Cl.$^7$ ..................... C07C 303/18; C07C 309/80; C07F 9/02
(52) U.S. Cl. .................... 562/834; 252/182.3; 540/579; 546/134; 546/181; 546/182; 546/348; 562/822; 564/82; 564/83
(58) Field of Search ...................... 252/182.3; 540/579; 546/134, 181, 182, 348; 562/822, 834; 564/82, 83

(56) References Cited

FOREIGN PATENT DOCUMENTS

| EP | 0 778 268 | 6/1997 | ......... C07C/313/06 |
| FR | 2 217 322 | 9/1974 | ......... C07C/143/72 |

OTHER PUBLICATIONS

J. Burdon, et al.: Journal of the Chemical Society, No. 6, Jun. 1957 pp. 2574–2578, ,XP000563885, Royal Society of Chemistry, Letchworth, GB.

A.P. Kozikowski et al.: Journal of the Chemical Society, Chemical Communications, No. 3, Feb. 1, 1988, pp. 198–200, XPO002109015, Royal Society of Chemistry, Letchworth, GB.

M. Kizil et al.: Tetrahedron Letters, vol. 37, No. 14, Apr. 1, 1996, XP004029981, Elsevier Science Publishers, Amsterdam, NL.

*Primary Examiner*—Peter O'Sullivan

(57) ABSTRACT

The present invention relates to a process and a reagent useful for the synthesis of sulphanilide which is perhalogenated on the carbon borne by the sulphur atom of the sulphanilide function. This persulphonylation process is characterized in that it comprises a step of placing a nucleophile, whose nucleophilic atom is a nitrogen, in contact with a reagent comprising, for successive or simultaneous addition, a heavy halide of sulphonyl, advantageously sulphonyl chloride, and an organic base comprising a trivalent atom from column V whose lone pair is conjugated directly or indirectly to a bond, and in that the organic part of the said sulphonyl is perhalogenated, advantageously perfluorinated, on the carbon borne by the sulphur. Application to the synthesis of intermediates for organic chemistry.

5 Claims, No Drawings

PROCESS AND REAGENT USEFUL FOR THE SYNTHESIS OF SULPHANILIDE WHICH IS PERHALOGENATED ON THE CARBON BORNE BY THE SULPHUR ATOM OF THE SULPHANILIDE FUNCTION

This application is a continuation application of application Ser. No. 09/433,436 filed on Nov. 4, 1999 now U.S. Pat. No. 6,271,419.

The present invention relates to a process for sulphonylating various nucleophiles, in particular nitrogenous nucleophiles. The invention relates more particularly to the sulphonylation of amines and more particularly anilines in the broad sense, i.e. amines linked to an aromatic ring.

The reaction is also directed towards a perhalosulphonylating reagent. Thus, the present invention relates more particularly to a sulphonylation reaction of an amine bearing an electron-withdrawing radical, especially when its amino functions are made soft, for example by the presence of an aryl radical (the amine then falling into the sub-category of anilines). The present invention is also directed towards the perhalosulphonylation of the very specific amine which is ammonia, to give either the amide or the imide.

The synthesis of these derivatives of sulphonamide type is often difficult, especially when the starting material used is a sulphonyl halide. Direct reactions usually fail, in particular with sulphonyl chlorides, especially when the organic part of the sulphonyls is highly electron-withdrawing, as is the case in particular when the atom bearing the sulphur of the sulphonyl function is perhalogenated, and more particularly when it is perfluorinated.

The explanation for these failures appears to be associated with the oxidizing nature of sulphonyl halides, in particular of trifluoromethanesulphonyl halides, which, like sulphuryl chloride, is an efficient oxidizing agent.

Accordingly, one of the aims of the present invention is to provide a process for obtaining sulphonamides of the above type using sulphonyl halides, in particular when these halides are heavy halides (i.e. halides corresponding to a halogen with an atomic number at least equal to that of chlorine).

It is preferred to use sulphonyl chlorides, for both economic and technical reasons. The technique has also been transposed to the synthesis of perfluorosulphonimides.

These aims and others which will become apparent hereinbelow are achieved by means of a sulphonylation process comprising a step of placing a nucleophile, whose nucleophilic atom is a nitrogen, in contact with a reagent comprising, for successive or simultaneous addition:

a heavy halide (i.e. a halide whose atomic number is at least equal to that of chlorine), of sulphonyl, advantageously sulphonyl chloride, and an organic base comprising a trivalent atom from column V (the nitrogen column in the Mendeleev table), the lone pair of this atom being conjugated directly or indirectly to a bond linking two atoms, at least one of which is an atom from column V, and by the fact that the organic part of the said sulphonyl is perhalogenated, advantageously perfluorinated, on the carbon borne by the sulphur.

The present invention is particularly advantageous for nucleophiles whose conjugate acid has a pKa of not more than about 7, advantageously not more than 6, preferably not more than 5, more preferably not more than 4. It is also advantageous for the oxidizable nucleophiles, and more generally when it is desired to use an oxidizable reagent.

The reason for this is that these nucleophiles are generally particularly difficult to sulphonylate. In particular, the invention is advantageous for nucleophiles whose nitrogen is linked to an electron-withdrawing group.

This electron-withdrawing group can be chosen in particular from aryls, advantageously electron-depleted aryls, and sulphonyls.

The said organic base comprising a trivalent atom from column V whose lone pair is conjugated to a bond can be used either as a base or as a catalyst for the reaction.

The reason for this is that the sulphonylation reaction releases a halohydric acid which salifies the nucleophile and makes the nucleophile more or less inert. Thus, it is desirable to add bases (in quantity and in nature) which will make it possible to release the nucleophile from the various acids present in the reaction medium such that it can act fully as a nucleophile.

The said organic base comprising a trivalent atom from column V conjugated to a bond is such that the said trivalent atom from column V is a trisubstituted atom and it forms a tertiary base.

According to one particularly advantageous embodiment of the present invention, the said bond linking two atoms is the bond of an imine function.

It is preferable for this imine function to be arranged such that the nitrogens are as far apart as possible, in other words such that the nitrogen of the imine function is that of the two atoms linked via the bond which is furthest from the trivalent atom from column V. That which has just been stated regarding the imine function is general for all the atoms from column V linked via the bond, when the bond comprises a carbon atom and an atom from column V.

According to the present invention, it is preferable for the organic base comprising a trivalent atom from column V, whose lone pair is conjugated to a bond, to have a sequence or skeleton of formula >N—(C=C)$_n$—C=N— with n=0 or an integer chosen in the closed range (i.e. comprising the limits) 1 to 4, advantageously from 1 to 3, preferably from 1 to 2. Preferably, the above sequence corresponds to the formula >N—(C(R$_1$)=C(R$_2$))n—C(R$_3$)=N— with n=0 or an integer chosen in the closed range (i.e. comprising the limits) 1 to 4, advantageously from 1 to 3, preferably from 1 to 2, and in which R$_1$, R$_2$ and R$_3$, which may be identical or different, are chosen from hydrocarbon-based derivatives, advantageously alkyl derivatives containing not more than 4 carbon atoms, and hydrogen. Advantageously, according to the process, the said trivalent atom from column V forms or constitutes a tertiary amine.

More specifically, it is desirable for the said organic base comprising a trivalent atom from column V, whose lone pair is conjugated to a bond, to constitute a molecule of the following formula (R$_5$)(R$_4$)N—(C(R$_1$)=C(R$_2$))$_n$—C=N—R$_6$ with n=0 or an integer chosen in the closed range (i.e. comprising the limits) 1 to 4, advantageously from 1 to 3, preferably from 1 to 2, and in which R$_1$, R$_2$ and R$_6$, which may be identical or different, are chosen from hydrocarbon-based groups, advantageously alkyl groups containing not more than 4 carbon atoms, and hydrogen, and in which R$_4$ and R$_5$, which may be identical or different, are chosen from hydrocarbon-based groups, advantageously alkyl groups containing not more than 4 carbon atoms, one or two of the substituents R$_1$, R$_2$, R$_3$, R$_4$, R$_5$ and R$_6$ being able to be linked to other substituent(s) remaining to form one or more rings.

The observed catalytic effect is particularly pronounced when the said bond linking two atoms is endocyclic, especially when it is endocyclic in an aromatic ring. This is particularly the case for pyridine rings and rings derived therefrom such as quinoline or isoquinoline.

The organic base comprising a trivalent atom from column V whose lone pair is conjugated to a bond can advantageously be dialkylaminopyridines in particular in the para- or ortho-position (i.e. in position 2 or 4 of the pyridine); diazobicycloundecen (DBU) also gives an advantageous result.

Although the present invention can be used to form common sulphonimides, this reaction is particularly advantageous in the case of the formation of an amide or imide function starting with a nucleophilic substrate, in particular one consisting of an aniline, and more particularly when this aniline is linked to an electron-depleted aromatic ring.

This depletion can be correlated to the introduction of a hetero atom into the ring (in the case of 6-membered rings) or to the presence, on the ring bearing the aniline function to be sulphonylated, of substituent(s) which are electron-withdrawing overall.

In the case of an electronic depletion of a 6-membered ring by means of the introduction of a hetero atom, it should be pointed out that the substrate, or more specifically the substrates, can be autocatalytic, i.e. they may not require the presence of an amine according to the present invention.

As regards depletion by the substituents, it may be indicated as a guide that the invention is particularly suitable for treating arylamines in which the substituents, excluding the nucleophilic function to be sulphonylated, of the ring bearing the nucleophilic atom are such that the sum of their Hammett $\sigma_p$ constants is at least equal to 0.14, advantageously to 0.20, preferably to 0.30.

When this sum of the Hammett constants reaches values of greater than 1, the reaction becomes particularly sluggish, and as such it is preferable for the sum of the Hammett constants for the ring bearing the amine function to be not more than 1, preferably not more than 0.9, more preferably not more than 0.7.

When the organic base comprising a trivalent atom from column V whose lone pair is conjugated, directly or indirectly, to a bond is used as catalyst (i.e. it is used in sub-stoichiometric amounts, more generally in an amount of between 1°/∞ and ⅕ of the stoichiometric amount, advantageously between ¹⁄₁₀₀ and ¹⁄₁₀ of the stoichiometric amount), it is then convenient to provide another base such that the reaction with respect to the nucleophilic substrate is as complete as possible.

In this case, the reagent used also comprises, for successive or simultaneous addition, an organic base, preferably one which cannot be alkylated. Non-alkylatable organic bases which may be chosen in particular are bulky dialkylphosphines, trialkylphosphines, phosphonium hydroxides, bulky dialkylamines, trialkylamines and ammonium hydroxides. The notion of bulkiness of bulky dialkylphosphines or dialkylamines such that they cannot be alkylated is well known to those skilled in the art.

In a great many cases, and in particular when solvents are used- it is preferable for the said non-alkylatable base to be liposoluble and to have at least one solubility in benzene which is significant (symbol "s" in the "Handbook of Chemistry and Physics"), and advantageously high (symbol "v" in the "Handbook of Chemistry and Physics").

As has been seen previously, it is usually desirable to carry out the placing in contact in an organic solvent. This solvent is advantageously relatively non-polar and preferably relatively immiscible with water. More particularly, it is desirable for not more than 10% by mass, advantageously not more than 5% and preferably not more than 2% by mass, to be miscible with water.

The amounts of base to be added and the amount of non-alkylatable base used during the reaction is advantageously at least equal to the amount required to neutralize the hydrohalic acid released.

In other words, the amount of base must be sufficient to ensure that the nucleophile is always present in free form (i.e. in true nucleophilic form) throughout the reaction.

The techniques towards which the present invention is directed are particularly suited to sulphonylation with perfluorinated alkylsulphonyl chlorides, which are perfluorinated in particular on the carbon borne by the sulphur.

The chloride which can most commonly be used is triflyl chloride ($CF_3SO_2Cl$). More generally, the organic part of the sulphonyl chloride corresponds to the formula (Rf).

Rf means a radical of formula:

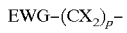

$$EWG-(CX_2)_p-$$

in which the groups X, which may be identical or different, represent a chlorine, a fluorine or a radical of formula $C_nF_{2n+1}$ where n is an integer of not more than 5, preferably not more than 2, with the condition that at least one of the groups X is fluorine;

in which p represents an integer of not more than 2;

in which EWG represents an electron-withdrawing group whose possible functions are inert under the reaction conditions, advantageously fluorine or a perfluoro residue of formula $C_nF_{2n+1}$ with n being an integer of not more than 8, advantageously not more than 5.

The total number of carbons in Rf is advantageously between 1 and 15, preferably between 1 and 10.

The present invention is also directed towards a reagent which is useful for carrying out the process according to the invention. This reagent comprises, for successive or simultaneous addition:

a heavy halide (i.e. a halide whose atomic number is at least equal to that of chlorine), of sulphonyl, advantageously sulphonyl chloride, and:

an organic base comprising a trivalent atom from column V (the nitrogen column) whose lone pair is conjugated directly or indirectly to a π bond linking two atoms, at least one of which is an atom from column V; the organic part of the said sulphonyl being perhalogenated, advantageously perfluorinated, on the carbon borne by the sulphur.

The reagent according to the present invention can also comprise, again for successive or simultaneous addition, a solvent. This solvent, including a mixture of solvents, is advantageously relatively non-polar and chosen from those which have low solubility in water. In certain cases, chlorinated aliphatic chains are not satisfactory.

As a touchstone for the polarity, it may be pointed out that the said relatively non-polar solvent is chosen from those, or mixtures of those, whose polarity ($E^f_t$ expressed in kcal/mol) is not more than 40 (advantageously to two significant figures).

These relatively non-polar solvents are usually chosen from oxygenated organic compounds, in particular ethers, esters or even ketones, hydrocarbons, including petroleum fractions, and aromatic hydrocarbons which are generally halogenated. The latter solvents are particularly advantageous, in particular substituted benzenes and hydrocarbons which are halogenated on the ring.

That which has just been described above is particularly suitable for anilines, in particular those in which the said nitrogen atom is linked to a 6-membered aromatic ring, preferably a homocyclic ring, preferably a non-fused benzenic ring, are advantageously electron-depleted as has already been pointed out above. Overall, given the possible substituents, the process of the instant invention is particularly suited to amines linked to an aryl whose electron-richness is not more than that of a para-chlorophenyl (richness evaluated by means of the Hammett sigma $\sigma_p$ constants).

Among the electron-withdrawing groups which are most commonly used, mention may be made of halogens (chlorine and fluorine), esters (of CO—OR type), ketones, amides not liable to interfere with the sulphonylation, alkyls which are perhalogenated on the carbon linked directly to the ring, in particular alkyls which are perfluorinated on the atom next to the ring, nitrites, and groups containing a sulphone or phosphone function directly linked to the ring.

The technique is directed especially to the sulphonylation of anilines in the broad sense (i.e. amines borne by an aryl), but this teaching has also been transposed to the sulphonamidation of (aqueous) ammonia and the sulphimidation of sulphamides. The technique is also directed especially to the double sulphonylation of ammmonia to obtain directly the corresponding sulphimide.

In this case, the latter are advantageously in the form of a salt of a non-alkylatable organic base (it is the base which is non-alkylatable).

Under these conditions, the nitrogen bears a hydrogen or, more preferably, a negative charge (anion), whereas, in the case of anilines which has been targeted above, the aniline function comprises at least one hydrogen, preferably two, for reasons of steric hindrance.

The use of the said organic base comprising a trivalent atom from column V whose lone pair is conjugated to a π bond makes it possible to carry out, in good yield, the double sulphonylation of nucleophiles which can be substituted twice (such as ammonia and primary amines). The preferred operating conditions are those described in the international patent application cited by reference and published by WIPO under the No. WO 98/52886, using, at least partially as base, the said organic base comprising a trivalent atom from column V whose lone pair is conjugated to a π bond.

For reasons of work hygiene, chlorinated aliphatic derivatives are generally to be avoided, although they constitute a family of solvents which gives good results, even though it is not the family which gives the best performance, since their solubility, and in particular that of methylene chloride, is of the order of 2% by volume, i.e. 2.6% by weight.

As regards the solvents, solvents with a reducing nature should be avoided as much as possible.

The reaction can be carried out from −20 to about 200° C., more generally from 0° to about 100° C.

It is easier to work at ambient temperature and pressure, but it is also possible to be at different, higher pressures. It is also possible to work in a closed chamber (such as an autoclave or sealed tube) and under autogenous pressure.

The non-limiting examples below illustrate the invention.

EXAMPLES

Preparation of 5-acetamido-2,4-dimethyltrifluoromethanesulphonanilide

Reaction in the Presence of a Catalyst:

350 g of dichloromethane, 50.1 g of 5-amino-2,4-dimethylacetanilide and 6.9 g of 4-dimethylaminopyridine are successively loaded into a reactor. The suspension obtained is then stirred and cooled to 10° C. 57.4 g of triethylamine are then added over 15 min at 10° C.

A solution of 56.8 g of trifluoromethanesulphonyl chloride in 59 g of dichloromethane is then added over 2 h while keeping the temperature of the medium at 10° C.

The medium is then kept stirring for 2 h at 10° C. and is then allowed to warm to a temperature of 20° C. and stirring is continued for 2 h.

The medium is acidified in the reactor by addition of 265 g of aqueous 4.2% HCl solution.

The precipitate formed is then filtered off and rinsed (3 times) with deionized water and then with dichloromethane. It is then dried at 95° C. under reduced pressure.

67 g of a beige solid are thus obtained, i.e. an isolated yield of 77%.

Characteristic of the compound: melting point=180° C.

Reaction in the Absence of Catalyst:

The above conditions are repeated, but in the absence of 4-dimethylaminopyridine.

Analysis of the reaction medium shows a 90% degradation of the trifluoromethanesulphonyl chloride.

Yield of expected product very much less than 10%.

Preparation of Methyl 5-chloro-2-(N-trifluoromethylsulphonyl)aminobenzoate

Reaction in the Presence of a Catalyst:

17 g of methyl 5-chloroanthranilate, 120 g of dichloromethane, 2.26 g of 4-dimethylaminopyridine and then 18.5 g of trifluoromethanesulphonyl chloride are successively loaded into a reactor. The solution is stirred at 15° C. and a solution of 18.7 g of triethylamine in 19 g of dichloromethane is added over 3 h. After addition, the medium is stirred for 3 h at 15° C. and then for 10 h at room temperature.

The medium is then washed successively with 150 g of deionized water, with 100 g of concentrated hydrochloric acid solution and then again with 160 g of deionized water.

The solvent is removed under reduced pressure. 27.7 g of a yellowish solid are thus obtained, i.e. a crude isolated yield of 95%.

Characteristic of the compound: melting point=81° C.

Reaction in the Absence of Catalyst:

1/ Reaction with triethylamine:

The above conditions are repeated, but in the absence of 4-dimethylaminopyridine.

Analysis of the reaction medium shows a total degradation of the trifluoromethanesulphonyl chloride.

The expected product was not formed.

2/ Reaction with diisopropylethylamine:

In the same manner, the test in the absence of catalyst and in the presence of diisopropylethylamine does not lead to the expected product.

3/ Reaction with 1,4-diazabicyclo[2,2,2]octane or DABCO:

Again, the expected product is not formed.

Preparation of Trialkylammonium Bis (trifluoromethanesulphonimide)

Catalysed Reaction:

Example 1

9.3 g of triethylamine (0.092 M), 0.56 g of 4-dimethylaminopyridine and 45 g of dichloromethane are loaded into a reactor. 1.38 g (0.092 M) of ammonia are then added. The solution obtained is stirred at 0° C.

Trifluoromethanesulphonyl chloride (15.5 g, i.e. 0.092 M) diluted in 10 ml of dichloromethane is then added over 2 h at 0° C, after which the reaction is continued for 3 h at room temperature.

Analysis of the reaction medium shows a trifluoromethanesulphinate impurity content of 2%.

The reaction medium is treated twice with 15 ml of aqueous 12% HCl solution and then 3 times with 15 ml of water. The residual organic phase is concentrated under reduced pressure, which thus gives 13.65 g of triethylammonium bis(trifluoromethanesulphonimide) in liquid form, equivalent to an isolated yield of 80%. The purity of the compound obtained is 98%.

Example 2

The procedure of Example 1 is repeated, but replacing the dichloromethane with dioxane. The reaction medium is analysed after dilution with water: the yield of bis (trifluoromethanesulphonimide) at the end of the reaction is 51% with a trifluoromethanesulphinate content of 6%.

Non-catalysed Reaction:

Comparative Example 3

The procedure of Example 1 is repeated, but without using 4-dimethylaminopyridine.

The yield of bis(trifluoromethanesulphonimide) at the end of the reaction is 47%, with a trifluoromethanesulphinate content of 21%.

Comparative Example 4

Procedure 3 is repeated, but using diisopropyl ethylamine as base in replacement for the triethylamine.

The yield of bis(trifluoromethanesulphonimide) at the end of the reaction is 51%, with a trifluoromethanesulphinate content of 21%.

Comparative Example 5

11.8 g of trifluoromethanesulphonyl chloride (0.07 M) are loaded into a reactor and 33.9 g of triethylamine (0.0336 M) are then added at 0° C. over 10 min.

The medium is stirred for a further 10 min at 0° C., followed by addition of 0.5 g of ammonia (0.029 M). The reaction is exothermic. The medium is then maintained at 65° C. for 4 h.

Compounds resulting from the oxidative degradation of the amines are observed. The major product is the trifluoromethanesulphinate in a content of 57%.

The presence of bis(trifluoromethanesulphonimide) is not revealed, which implies a reaction yield of less than 2%, or even zero.

What is claimed is:

1. A reagent for carrying out a sulphonylation process for the preparation of a sulphonated product comprising the steps of:

1) reacting a nitrogen nucleophile with a reagent, said reagent comprising:
      a sulphonyl halide having an organic part and whose halogen atom has an atomic number at least equal to that of chlorine,
      an organic base comprising a trivalent atom from column V whose lone pair is conjugated, directly or indirectly, to a bond linking two atoms, at least one of which is an atom from column V, and
      the organic part of said sulphonyl being perhalogenated on the carbon borne by the sulphur; and 2) recovering the sulphonated product thus formed; said reagent comprising:
      a sulphonyl halide having an organic part and whose halogen atom has an atomic number at least equal to that of chlorine the organic part of said sulphonyl being perfluorinated, on the carbon borne by the sulphur, and
      an organic base comprising a trivalent atom from column V whose lone pair is conjugated directly or indirectly to a π bond linking two atoms, at least one of which is an atom from column V.

2. A reagent according to claim 1, further comprising a solvent which is relatively non-polar, being not more than 10% by mass miscible with water in water, and containing no chlorinated aliphatic chain.

3. A reagent according to claim 2, wherein said relatively non-polar solvent has a polarity $E^f_t$ expressed in kcal/mol of not more than 40.

4. A reagent according to claim 2, wherein said relatively non-polar solvent is an oxygenated organic compound, a hydrocarbon, a petroleum fraction, or an aromatic hydrocarbon halogenated on the ring.

5. A reagent according to claim 2, wherein said relatively non-polar solvent is a substituted benzene.

* * * * *